(12) United States Patent
Zhu

(10) Patent No.: US 8,617,835 B2
(45) Date of Patent: Dec. 31, 2013

(54) POROUS PARTICLE REAGENT COMPOSITIONS, DEVICES, AND METHODS FOR BIOSENSORS

(75) Inventor: Boru Zhu, Granger, IN (US)

(73) Assignee: Bayer HealthCare LLC, Whippany, NJ (US)

( * ) Notice: Subject to any disclaimer, the term of this patent is extended or adjusted under 35 U.S.C. 154(b) by 0 days.

(21) Appl. No.: 13/555,421

(22) Filed: Jul. 23, 2012

(65) Prior Publication Data

US 2012/0305410 A1     Dec. 6, 2012

Related U.S. Application Data

(62) Division of application No. 12/331,817, filed on Dec. 10, 2008, now Pat. No. 8,252,523.

(60) Provisional application No. 61/012,739, filed on Dec. 10, 2007.

(51) Int. Cl.
*C12Q 1/54* (2006.01)
*C12Q 1/00* (2006.01)
*C12Q 1/26* (2006.01)
*C12N 11/14* (2006.01)

(52) U.S. Cl.
USPC ............. 435/14; 435/4; 435/25; 435/176; 204/403.14; 205/777.5

(58) Field of Classification Search
None
See application file for complete search history.

(56) References Cited

U.S. PATENT DOCUMENTS

| | | | |
|---|---|---|---|
| 4,312,834 A | 1/1982 | Vogel et al. | |
| 5,120,420 A | 6/1992 | Nankai et al. | |
| 5,393,615 A | 2/1995 | Corey et al. | |
| 5,498,542 A | 3/1996 | Corey et al. | |
| 5,520,786 A | 5/1996 | Bloczynski et al. | |
| 5,708,247 A | 1/1998 | McAleer et al. | |
| 5,798,031 A | 8/1998 | Charlton et al. | |
| 5,951,836 A | 9/1999 | McAleer et al. | |
| 6,531,040 B2 | 3/2003 | Musho et al. | |
| 6,841,609 B2 | 1/2005 | Chapman et al. | |
| 6,916,410 B2 | 7/2005 | Katsuki et al. | |
| 6,982,027 B2 | 1/2006 | Yagi | |
| 7,053,125 B2 | 5/2006 | Lewis et al. | |
| 7,964,372 B2 | 6/2011 | Marfurt | |
| 8,211,379 B2 | 7/2012 | Burke et al. | |
| 2003/0091647 A1 | 5/2003 | Lewis et al. | |
| 2007/0135698 A1 | 6/2007 | Shah et al. | |
| 2009/0099433 A1 | 4/2009 | Staib et al. | |
| 2009/0123955 A1 | 5/2009 | Marfurt | |
| 2009/0310743 A1 | 12/2009 | Carpenter et al. | |

FOREIGN PATENT DOCUMENTS

| | | |
|---|---|---|
| CN | 101058824 | 10/2007 |
| JP | 03160358 A * | 7/1991 |
| WO | 2004113902 | 12/2004 |
| WO | 2006065900 | 6/2006 |
| WO | 2006132294 | 12/2006 |
| WO | 2007013915 | 2/2007 |

OTHER PUBLICATIONS

WIPO, "International Search Report and Written Opinion for PCT/US2008/086162", "International Search Report", Feb. 17, 2009, Publisher: International Searching Authority.
Gunasingham, et al., "Pulsed amperometric detection of glucose using a mediated enzyme electrode", "Journal of Electroanalytical Chemisty", 1990, pp. 349-362, vol. 287, No. 2.

* cited by examiner

*Primary Examiner* — Jon P Weber
*Assistant Examiner* — Charles Zoltan Constantine

(57) ABSTRACT

A reagent composition for a biosensor sensor strip is disclosed that provides for rapid rehydration after drying. The composition includes porous particles and is preferably formed as a colloidal suspension. The dried reagent composition including porous particles may provide analytically useful output from the sensor strip in a shorter time period than observed from dried reagent compositions using solid particles. The output signal from the porous particle compositions may be correlated to the analyte concentration of a sample within about two seconds. In this manner, an accurate concentration determination of an analyte concentration in a sample may be obtained in less time than from sensor strips including conventional compositions. The reagent composition including the porous particles also may allow for the redox reaction between the reagents and the analyte to reach a maximum kinetic performance in a shorter time period than observed from conventional sensor strips.

24 Claims, 5 Drawing Sheets

POROUS PARTICLE REAGENT COMPOSITIONS, DEVICES, AND METHODS FOR BIOSENSORS

REFERENCE TO RELATED APPLICATIONS

This application is a division of U.S. application Ser. No. 12/331,817, filed Dec. 10, 2008, entitled "Porous Particle Reagent Compositions, Devices, and Methods for Biosensors", the contents of which are incorporated herein by reference; which claimed the benefit of U.S. Provisional Application No. 61/012,739 entitled "Porous Particle Reagent Compositions, Devices, and Methods for Biosensors" filed Dec. 10, 2007, which also is incorporated herein by reference.

BACKGROUND

Biosensors provide an analysis of a biological fluid, such as whole blood, serum, plasma, urine, saliva, interstitial, or intracellular fluid. Typically, biosensors have a measurement device that analyzes a sample residing in a sensor strip. The sample usually is in liquid form and in addition to being a biological fluid, may be the derivative of a biological fluid, such as an extract, a dilution, a filtrate, or a reconstituted precipitate. The analysis performed by the biosensor determines the presence and/or concentration of one or more analytes, such as alcohol, glucose, uric acid, lactate, cholesterol, bilirubin, free fatty acids, triglycerides, proteins, ketones, phenylalanine, or enzymes, in the biological fluid. The analysis may be useful in the diagnosis and treatment of physiological abnormalities. For example, a diabetic individual may use a biosensor to determine the glucose level in whole blood for adjustments to diet and/or medication.

Biosensors may be designed to analyze one or more analytes and may use different sample volumes. Some biosensors may analyze a single drop of whole blood, such as from 0.25-15 microliters (µL) in volume. Biosensors may be implemented using bench-top, portable, and like measurement devices. Portable measurement devices may be handheld and allow for the identification and/or quantification of one or more analytes in a sample. Examples of portable measurement devices include the Ascensia Breeze® and Elite® meters of Bayer HealthCare in Tarrytown, N.Y., while examples of bench-top measurement devices include the Electrochemical Workstation available from CH Instruments in Austin, Tex. Biosensors providing shorter analysis times, while supplying the desired accuracy and/or precision, provide a substantial benefit to the user.

In electrochemical biosensors, the analyte concentration is determined from an electrical signal generated by an oxidation/reduction or redox reaction of the analyte or a species responsive to the analyte when an input signal is applied to the sample. The input signal may be applied as a single pulse or in multiple pulses, sequences, or cycles. An oxidoreductase, such as an enzyme or similar species, may be added to the sample to enhance the electron transfer from a first species to a second species during the redox reaction. The enzyme or similar species may react with a single analyte, thus providing specificity to a portion of the generated output signal.

Electrochemical biosensors usually include a measurement device having electrical contacts that connect with electrical conductors in the sensor strip. In either case, the sensor strip may be adapted for use outside, inside, or partially inside a living organism. When used outside a living organism, a sample of the biological fluid is introduced into a sample reservoir in the sensor strip. The sensor strip may be placed in the measurement device before, after, or during the introduction of the sample for analysis. When inside or partially inside a living organism, the sensor strip may be continually immersed in the sample or the sample may be intermittently introduced to the strip. The sensor strip may include a reservoir that partially isolates a volume of the sample or be open to the sample. Similarly, the sample may continuously flow through the strip or be interrupted for analysis.

For electrochemical biosensors, the conductors may be made from conductive materials, such as solid metals, metal pastes, conductive carbon, conductive carbon pastes, conductive polymers, and the like. The electrical conductors typically connect to working, counter, reference, and/or other electrodes that extend into a sample reservoir. One or more electrical conductors also may extend into the sample reservoir to provide functionality not provided by the electrodes.

The sensor strip may be formed by disposing or printing electrodes on an insulating substrate using multiple techniques, such as those described in U.S. Pat. Nos. 6,531,040; 5,798,031; and 5,120,420. The electrodes may be formed by disposing one or more reagent composition on one or more of the conductors. More than one of the conductors may be coated by the same reagent composition, such as when the working and counter electrodes are coated by the same composition. Different reagent compositions may be disposed on the conductors. Thus, the reagent composition of the working electrode may contain the enzyme, the mediator, and a binder while the reagent composition of the counter electrode contains a mediator, which could be the same or different as the mediator of the working electrode, and a binder.

The reagent composition may include an ionizing agent for facilitating the oxidation or reduction of the analyte, such as an oxidoreductase, as well as any mediators or other substances that assist in transferring electrons between the analyte and the working electrode. In addition to binding the reagents together, the binder may assist in filtering red blood cells, preventing them from coating the conductor surface, and stabilizing the oxidoreductase, for example.

Multiple techniques known to those of ordinary skill in the art may be used to dispose the reagent composition on the sensor strip. The reagent composition may be disposed on the conductors and then dried. When the sample is introduced to the sensor strip, the reagent composition begins to rehydrate. The quicker the reagent composition rehydrates, the quicker an output signal from which the concentration of the analyte in the sample may be obtained. The sooner an output signal is obtained from the sensor strip, from which the concentration of the analyte may be accurately determined, the sooner the analysis may be completed. Thus, biosensors including reagent compositions providing shorter analysis times, while supplying the desired accuracy and/or precision, may provide a substantial benefit to the user.

SUMMARY

A reagent composition for a biosensor sensor strip is disclosed that provides for rapid rehydration after drying. The composition includes porous particles and is preferably formed as a colloidal suspension. The dried composition may provide analytically useful output from the sensor strip in a shorter time period than observed from dried compositions using solid particles. The output signal from the porous particle compositions may be correlated to the analyte concentration of a sample within about three seconds, preferably within about two seconds or less.

A reagent composition for determining the concentration of an analyte in a sample is described that includes about 1% to about 30% (w/w) of an about 20% to an about 50% (w/w)

suspension of porous particles, the particles having an average diameter from 0.05 micrometer to 10 micrometer and a void volume of at least 20% (v/v); about 0.1% to about 3% (w/w) of at least one polymeric material; and about 0.1 active unit to about 10 active units of at least one enzyme system per microliter of the reagent composition.

An electrode for a biosensor is disclosed that includes at least one conductor; and at least one reagent composition disposed on the conductor, the reagent composition including porous particles having an average diameter from 0.05 micrometer to 10 micrometer and a void volume of at least 20% (v/v); from about 0.5% to about 10% (w/w) of at least one mediator; at least one polymeric material; and at least one enzyme system.

A biosensor sensor strip for determining the concentration of an analyte in a sample is described that includes a sensor base at least partially covered by a lid; at least one reservoir formed by the sensor base, where the at least one reservoir encloses at least two conductors disposed on the base; at least one reagent composition on at least one of the conductors to form a working electrode, the at least one reagent composition including about 0.1 active unit to about 10 active units of at least one enzyme system per microliter of the at least one reagent composition; about 0.5% to about 10% (w/w) of at least one mediator; and at least one polymeric material, where the reservoir and the at least one reagent composition provide a maximum kinetic performance of a redox reaction of an analyte with the at least one reagent composition within less than about three seconds of introducing a sample to the sensor strip, and where the maximum kinetic performance is determined with a gated amperometric pulse sequence having at least five duty cycles, and where each excitation of the duty cycles is 0.4 second in duration, each relaxation of the duty cycles is one second in duration, the relaxations are provided by an open circuit, at least three output current values are measured during each excitation, the excitations have a substantially constant potential of 250 mV, and the sample temperature is 23° C.

A biosensor system for determining the concentration of an analyte in a sample is disclosed that includes a support means for supporting at least two conductors; a reaction means for selectively performing a redox reaction on an analyte, where the reaction means include at least one polymeric material; a measurement means for measuring a rate of redox of the analyte, where the measurement means includes at least two conductors; and where the measurement means measures a rate of the redox reaction at a maximum kinetic performance within less than about three seconds of introducing a sample to the reaction means, and where the maximum kinetic performance is determined with a gated amperometric pulse sequence having at least five duty cycles, and where each excitation of the duty cycles is 0.4 seconds in duration, each relaxation of the duty cycles is one second in duration, the relaxations are provided by an open circuit, at least three output current values are measured during each excitation, the excitations have a substantially constant potential of 250 mV, and the sample temperature is 23° C.

A method of determining the concentration of an analyte in a sample is described that includes introducing an aqueous sample including at least one analyte to a reagent composition, the reagent composition including porous particles having an average diameter from 0.05 micrometer to 10 micrometer and a void volume of at least 20% (v/v), and at least one polymeric material; rehydrating the reagent composition with the aqueous sample; applying an input signal to the aqueous sample; measuring at least one output signal current value within about 0.4 to about 5 seconds of introducing the aqueous sample to the reagent composition; and determining the concentration of the at least one analyte in the aqueous sample from the at least one output signal current value.

Other systems, methods, features and advantages of the invention will be, or will become, apparent to one with skill in the art upon examination of the following figures and detailed description. It is intended that all such additional systems, methods, features, and advantages be included within this description, be within the scope of the invention, and be protected by the claims that follow.

BRIEF DESCRIPTION OF THE DRAWINGS

The invention can be better understood with reference to the following drawings and description. The components in the figures are not necessarily to scale, emphasis instead being placed upon illustrating the principles of the invention.

DETAILED DESCRIPTION

A reagent composition for a biosensor sensor strip is disclosed that provides for rapid rehydration after drying. The composition includes porous particles and is preferably formed as a colloidal suspension. The porous particles have an average diameter from 0.05 to 10 micrometers, a void volume of at least 20% (v/v), and are preferably made of silica. The dried reagent composition including the porous particles may provide analytically useful output from the sensor strip in a shorter time period than observed from dried reagent compositions using solid particles. The reagent composition including the porous particles also may allow for the redox reaction between the reagents and the analyte to reach a maximum kinetic performance in a shorter time period than observed from dried reagent compositions using solid particles.

The output signal from the reagent compositions including porous particles may be correlated to the analyte concentration of a sample within about two seconds. This is a substantial improvement over conventional sensor strips using clays and other solid particles in the reagent composition, which may require more than four seconds to provide an output signal for correlation with the analyte concentration of the sample.

Figure 1A:
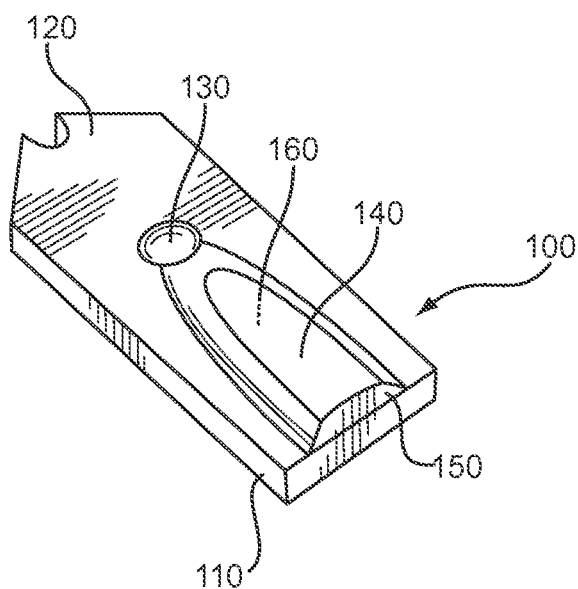
FIG. 1A is a perspective representation of an assembled sensor strip.
Figure 1B:
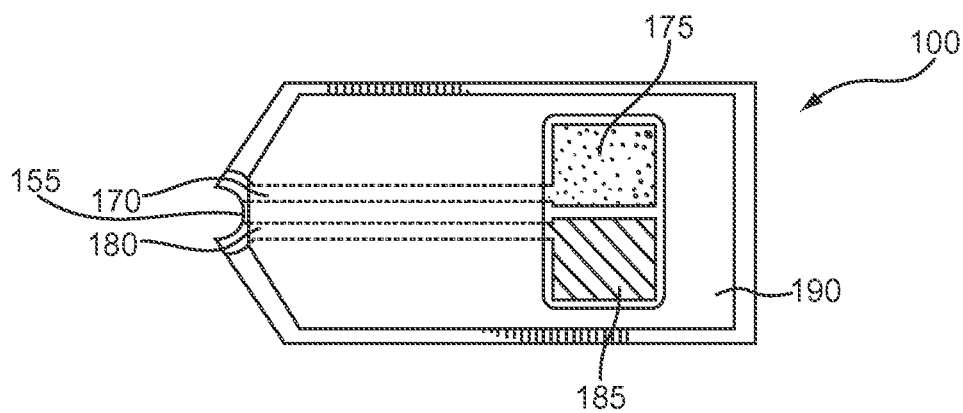
FIG. 1B is a top-view representation of a sensor strip, with the lid removed.

FIGS. 1A and 1B depict a sensor strip 100. FIG. 1A is a perspective representation of the assembled sensor strip 100 including a sensor base 110, at least partially covered by a lid 120 including a vent 130, a sample coverage area 140, and an input end opening 150. A partially-enclosed reservoir 160 is formed between the base 110 and the lid 120. Other sensor strip designs also may be used.

A liquid sample for analysis may be transferred into the reservoir 160 by introducing the liquid to the opening 150. The liquid fills the reservoir 160 while expelling the previously contained air through the vent 130. The reservoir 160 may contain a retention composition (not shown) that assists in retaining the liquid sample in the reservoir. Examples of retention compositions include water-swellable polymers, such as carboxymethyl cellulose and polyethylene glycol; and porous polymer matrices, such as dextran and polyacrylamide.

FIG. 1B represents a top-view of the sensor strip 100, with the lid 120 removed. Conductors 170 and 180 may run under a dielectric layer 190 from a measurement device interface 155 to a working electrode 175 and a counter electrode 185, respectively. The working and counter electrodes 175,185 may be in substantially the same plane, as depicted in the figure, or in different planes (not shown). The working and counter electrodes 175, 185 may be separated from an upper portion of the lid 120 by at least 100 μm. The dielectric layer 190 may partially cover the electrodes 175, 185 and may be made from any suitable dielectric material, such as an insulating polymer.

The counter electrode 185 may support the electrochemical activity at the working electrode 175 of the sensor strip 100. The potential to support the electrochemical activity at the working electrode 175 may be provided to the sensor system by forming the counter electrode 185 from an inert material, such as carbon, and including a soluble redox species, such as a ferricyanide mediator, within the reservoir 160. The potential at the counter electrode 185 may be a reference potential achieved by forming the counter electrode 185 from a redox pair, such as Ag/AgCl, to provide a combined reference-counter electrode. Alternatively, the sensor strip 100 may be provided with a third conductor and electrode (not shown) to provide a reference potential to the sensor system.

Figure 2:
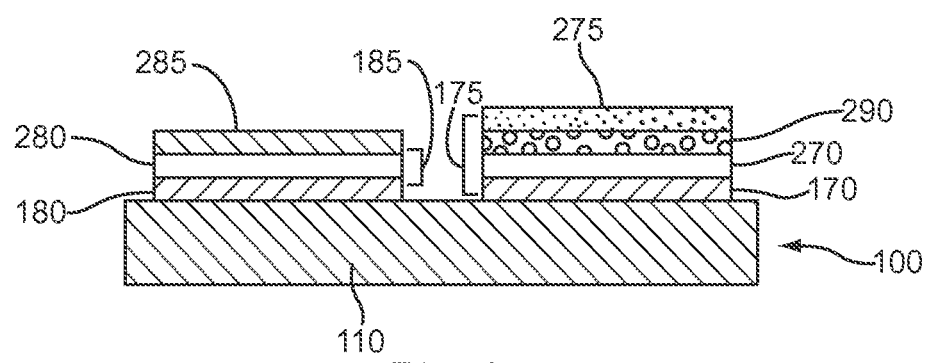
FIG. 2 is an end view representation of the sensor strip of FIG. 1B.

FIG. 2 represents an end-view diagram of the sensor strip of FIG. 1B showing the layer structure of the working electrode 175 and the counter electrode 185. The conductors 170 and 180 may be disposed directly on the base 110. Surface conductor layers 270 and 280 optionally may be disposed on the conductors 170 and 180, respectively. The surface conductor layers 270, 280 may be made from the same or from different materials as the conductors 170, 180.

The material or materials used to form the conductors 170, 180 and the surface conductor layers 270, 280 may include any electrical conductor. Preferable electrical conductors are non-ionizing, such that the material does not undergo a net oxidation or a net reduction during analysis of the sample. The conductors 170, 180 preferably include a thin layer of a metal paste or metal, such as gold, silver, platinum, palladium, copper, or tungsten. The surface conductor layers 270, 280 preferably include carbon, gold, platinum, palladium, or combinations thereof. If a surface conductor layer is not present on a conductor, the conductor is preferably made from a non-ionizing material.

The surface conductor material may be deposited on the conductors 170, 180 by any conventional means compatible with the operation of the sensor strip, including foil deposition, chemical vapor deposition, slurry deposition, and the like. In the case of slurry deposition, the mixture may be applied as an ink to the conductors 170, 180, as described in U.S. Pat. No. 5,798,031, for example.

The reagent layers 275 and 285 may be disposed near and/or on the conductors 170 and 180, respectively. The term "on" is defined as "above" and is relative to the orientation being described. For example, if a first element is deposited over at least a portion of a second element, the first element is said to be "on" the second. In another example, if a first element is present above at least a portion of a second element, the first element is said to be "on" the second. The use of the term "on" does not exclude the presence of substances between the upper and lower elements being described. For example, a first element may have a coating over its top surface, yet a second element over at least a portion of the first element and its top coating may be described as "on" the first element. Thus, the use of the term "on" may or may not mean that the two elements being related are in physical contact.

The reagent layers 275 and 285 are formed from at least one reagent composition that includes reagents and a binder. The binder includes substantially water-insoluble porous particles and at least one polymeric material that is substantially water-soluble. The porous particles provide additional physical structure to the polymeric material. The binder may form a gel or gel-like material when hydrated by the sample. An optional layer 290 may be disposed on the conductor 170 and/or the surface conductor 270. The optional layer 290 may lack one or more constituents of the reagent layer 275.

The reagent layers 275 and 285 may include the same or different reagents. When including the same reagents, the reagent layers 275 and 285 may be the same layer. When including different reagents, the reagents present in the first layer 275 may be selected for use with the working electrode 175, while the reagents present in the second layer 285 may be selected for use with the counter electrode 185. For example, the reagents in the layer 285 may include a mediator to facilitate the free flow of electrons between the sample and the conductor 180. Similarly, the reagents in the layer 275 may include an enzyme system and optionally a mediator to facilitate the reaction of the analyte.

The enzyme system included in the reagent layer 275 may be specific to the analyte and may facilitate the reaction of the analyte while enhancing the specificity of the sensor system to the analyte, especially in complex biological samples. The enzyme system may include one or more enzyme, cofactor, and/or other moiety that participates in a redox reaction with the analyte. For example, an alcohol oxidase can be used to provide a sensor strip that is sensitive to the presence of alcohol in a sample. Such a system could be useful in measuring blood alcohol concentrations. In another example, glucose dehydrogenase or glucose oxidase may be used to provide a sensor strip that is sensitive to the presence of glucose in a sample. This system could be useful in measuring blood glucose concentrations, for example in patients known or suspected to have diabetes.

The reagent layers 275, 285 may be deposited by any convenient means, such as printing, liquid deposition, or ink-jet deposition. Factors, such as the viscosity of the material being applied as well as the screen-size and emulsion combination, may affect the resulting thickness of the reagent layers 275, 285. When thinner reagent layers are preferred, deposition methods other than printing, such as micro-pipetting, ink jetting, or pin-deposition, may be used. These deposition methods generally give the dry reagent layers a micrometer or sub-micrometer thickness, such as 1-10 μm. For example, pin-deposition methods may provide average reagent layer thicknesses of 1 μm. The thickness of the reagent layer resulting from pin-deposition, for example, may be controlled by the amount of polymeric material and porous particles included in the reagent composition, with higher binder content providing thicker reagent layers.

After deposition on the sensor strip, the reagent composition may be dried to form the reagent layers 275, 285. During drying, the porous particles are believed to maintain space between the constituents of the suspension and reduce the tendency of the composition to create a closely packed structure, thus, forming a structure similar is physical characteristics to a sponge. On rehydration, water and the analyte, such as glucose, may rapidly enter the pores to rehydrate the composition. It is believed that the pores of the particles provide for water to access the interior regions of the dried composition more quickly than when a non-porous material is used. Thus, the physical structure and the constituents in the dried reagent composition affect the rate at which an aqueous sample can rehydrate the one or more reagent layers of the sensor strip.

In addition to providing pathways through the dried reagent composition, the pores also may substantially increase the surface area of one or more of the reagent constituents initially contacted by the sample. For example, mediator would be more rapidly exposed to the sample by adsorbing the mediator throughout the pores of the particles than by drying the mediator on the exterior of solid particles.

It is believed that either the pathways through and/or the increased surface area exposure of the reagents of the dried reagent composition including porous particles may increase the rate at which the reagents of the reagent composition rehydrate to provide an output signal for correlating with the analyte concentration of the sample. Furthermore, the porous particles may extend the shelf-life of the sensor strips by reducing the separation of some of the reagent composition constituents. This reduction in constituent separation is thought to better stabilize the active enzyme system, thus reducing denaturization.

A preferred reagent composition may be provided by combining the substantially insoluble porous particles, a polymeric material, a buffer, a surfactant, a mediator, and an enzyme system. Preferred reagent compositions also may be provided that exclude one or both of the mediator and the enzyme system. Water may then be added to form a colloidal suspension having the desired stability. The reagent composition may include fewer or additional constituents.

The reagent composition preferably includes from about 1 to about 30% (w/w) of an about 20 to about 50% (w/w) suspension of the porous particles in water. More preferably, the composition includes from about 2 to about 15% of an about 20 to an about 35% (w/w) suspension of the porous particles in water. At present, an especially preferred reagent composition includes from about 4 to about 8% of an about 23 to an about 28% (w/w) suspension of the porous particles in water. Preferably, a ratio of about 1:10 (w/w) is maintained between the porous particle suspension and the polymeric material. Other ratios may be used to provide different viscosities to the reagent composition. It is believed that the change in the morphology of the colloid provided by the varying ratios of porous particles to the polymeric material may be attributed to hydrogen bonding effects.

Preferable porous particles for inclusion in the reagent composition include porous particles having average particle diameters preferably from 0.05 to 10 micrometers (μm), more preferably from 0.1 to 5 μm. At present, especially preferred average diameters for the porous particles are from 0.1 to 0.5 μm. For example, a mixture of porous particles having average diameters from 0.1 to 1 μm, with an average diameter of 0.3 μm for the mixture, would be especially preferred at present. The porous particles are made from one or more material. Particle diameters may be determined using laser scattering, such as with a LA930 instrument available from Horiba Instruments, Inc., Irvine, Calif.

Preferably, porous particles for inclusion in the reagent composition have void volumes of at least 20% (v/v) and more preferably, at least 40% (v/v). At present, especially preferred particles have void volumes of at least 65% (v/v). The void volume of a porous particle or particles may be determined by determining the volume held within the pores of the particle in relation to the volume of the particle, such as may be determined by gas adsorption (e.g. BJH nitrogen porosimetry) or mercury porosimetry.

The particles may have an average pore volume from about 0.5 to about 1 milliliter per gram (mL/g), more preferably from about 0.65 to about 0.85 mL/g. Preferably, at least about 0.5 cubic centimeter per gram (cc/g), more preferably at least about 0.7 cc/g or 0.9 cc/g, of the pore volume is from pores having a pore size of 600 angstroms (A) or less. These viscosity derived pore volumes may be determined as described in U.S. Pat. No. 6,841,609, for example. At present, especially preferred porous particles have at least 80% of the pore volume from pores having pore sizes of less than 300 A. The porous particles may have an average surface area from about 100 to about 200 meter$^2$ per gram (m$^2$/g), more preferably from about 140 to about 180 m$^2$/g. At present, porous particles having an average surface area from about 155 to about 175 m$^2$/g are especially preferred, such as the silica porous particle slurries SYLOJET 733A (anionic) or 733C (cationic) by Grace Davison, Columbia, Md.

While the material from which the porous particles are made may be any material compatible with the deposition and analysis that is substantially insoluble in aqueous solutions, particles made from inorganics, such as silica and zeolite, are presently preferred. Silica is presently more preferred. Materials that allow the porous particles to support a charge in aqueous media are preferred. The material may provide a negative charge, such as silica, or a positive charge, such as a zeolite. Silica also may be modified to provide a positive charge, such as zeta potentials of at least +20 mV or more preferably at least +40 mV. Preferably, the average diameter and material from which the porous particles are made provide for the formation of a colloid when the particles are suspended in water. In addition to inorganics, organic, ceramic, and other materials that are substantially insoluble in water also may be used.

Unlike the other components of the reagent composition, such as substantially water-soluble polymers, buffers, surfactants, water-soluble mediators, and the enzyme system, the porous particles are substantially insoluble in water. Solutions, unlike colloidal suspensions, lack an identifiable interface between the solubilized molecules and the solvent. In solutions, the solubilized molecules are in direct contact with the solvent, while in colloidal suspensions it is the surface of the particles that are in direct contact with the carrier liquid. Hence, the carrier liquid does not solubilize the porous particles that make up a colloid; instead, the carrier liquid "carries" the particles. By carrying the particles, a suspension results.

The interfaces between the suspended porous particles, and the carrier liquid or liquid mixture in which they reside, play a dominant role in determining the behavior and capabilities of the colloidal suspension forming the reagent composition. Colloidal suspensions are considered stable if the particles that form the colloid are separated or deflocculated, e.g., not aggregated or flocculated. In general, the term stability in relation to colloidal suspensions relates to the suspension's resistance to change over time.

Long-range attractive forces, such as van der Waals forces, are believed to pull the particles together. When colloidal particles are pulled together, the colloidal suspension is destabilized. This destabilization is often referred to as aggregation or flocculation and can result in precipitation of the aggregated particles from the colloidal suspension. Alternatively, columbic, steric, and other repulsive interactions are believed to repel colloidal particles from each other. If the particles cannot aggregate together, the stability of the colloidal suspension is increased and flocculation may be reduced. A colloidal suspension is stabilized against flocculation when at least 90% (w/w) of the particles can be observed as being individual, rather than aggregated in groups of two or more. This determination is made by diluting the suspension to 1 part-per-million particles, placing the diluted suspension on a slide, and observing by light microscopy.

Preferably, the reagent composition is formed as a colloidal suspension with varying amounts of the porous particles in water. More preferably, the reagent composition is formed as a colloidal suspension stabilized against flocculation. The preferred quantity of particles which should be added to form a colloidal suspension to yield the desired viscosity for the reagent composition is dependent on the nature of the particles, the polarity of the carrier liquid, and the charge carried by the particles at the pH of the reagent composition. In addition to the quantity of particle addition and the amounts and nature of the other reagent composition constituents, the material or materials from which the particles are formed also may be changed to produce less or more stabilization at similar volume amounts, depending on the carrier liquid.

The reagent composition preferably includes from about 0.1 to about 10% (w/w) of a polymeric material, more preferably from about 0.8 to about 3% (w/w). At present, an especially preferred reagent composition includes from about 1 to about 1.5% (w/w) of the polymeric material. Suitable substantially water-soluble polymeric materials for use as the binder may include poly(ethylene oxide) (PEO), carboxy methyl cellulose (CMC), polyvinyl alcohol (PVA), hydroxyethylene cellulose (HEC), hydroxypropyl cellulose (HPC), ethyl hydroxyethyl cellulose, carboxymethyl ethyl cellulose, polyvinyl pyrrolidone (PVP), polyamino acids, such as polylysine, polystyrene sulfonate, gelatin, acrylic acid, methacrylic acid, maleic anhydride salts thereof, derivatives thereof, and combinations thereof. Polymeric materials include monomers, pre-polymers, and other materials that form or have repeating units. Other polymeric materials may be used.

Among these polymeric materials, PEO, PVA, CMC, and HEC are preferred, with PVA being more preferred at present. For PVA, weight average molecular weights (Mw) from about 8,000 to about 1,000,000 are preferred, with Mw from about 15,000 to about 250,000 being more preferred. At present, PVA having a Mw of about 30,000 to about 50,000 is especially preferred.

The reagent composition preferably includes from about 0.01 to about 1% (w/w) of a surfactant, more preferably from about 0.01 to about 0.5% (w/w). At present, from about 0.03 to about 0.2% (w/w) of a surfactant is especially preferred. The surfactant can be any surfactant that assists in the formation of a colloidal suspension of the desired viscosity and stability and that is compatible with the deposition method and analysis. At present, saccharide based surfactants, such as N-octanoyl-N-methyl-D-glucamine (sold as MEGA 8 and available from DOJINDO, Gaithersburg, Md.) are preferred. This surfactant includes approximately eight oxyethylene units per molecule, for example. Other preferred surfactants are the ethoxylate based neutral surfactants, such as the PEG-30 tetramethyl decynediol surfactants (SURFYNOL 485, for example, as available from Air Products, Allentown, Pa.). Surfactants that increase the sample fill rate of the sensor strip and/or assist in stabilizing the enzyme system are preferred.

The reagent composition preferably includes a buffer to maintain the pH of the colloidal suspension from about 4.5 to about 7.5, more preferably from about 5 to about 7. The preferred pH and buffer or buffers for the reagent composition may be chosen to maintain the activity of the enzyme. Citrate based buffers are presently preferred, but others may be used. The concentration of buffer introduced to the reagent composition may range from about 10 to about 100 millimolar (mM). Buffer solutions having other concentrations may be used.

The reagent composition may include a one or two electron substantially water-soluble mediator. Mediators may be separated into two groups based on their electrochemical activity. One electron transfer mediators are chemical moieties capable of taking on one additional electron during the conditions of the electrochemical reaction, while two electron transfer mediators are chemical moieties capable of taking on two additional electrons during the conditions of the reaction. When a one electron transfer mediator, such as ferricyanide, is used, from about 0.5 to about 10% (w/w) is preferred, with from about 1.5 to about 2.5% (w/w) being more preferred. Examples of one electron transfer mediators include compounds, such as 1,1'-dimethyl ferrocene, ferrocyanide and ferricyanide, and ruthenium(III) and ruthenium(II) hexaamine.

While other mediators may be used, two electron transfer mediators may be preferred for their ability to transfer approximately twice as many electrons from the enzyme system to the working electrode for the same molar amount of mediator in relation to one electron transfer mediators. Thus, in comparison to one electron transfer mediators, smaller amounts of two electron transfer mediators may be used in the reagent composition.

Examples of two electron transfer mediators include the organic quinones and hydroquinones, such as phenathroline quinone; phenothiazine and phenoxazine derivatives; 3-(phenylamino)-3H-phenoxazines; phenothiazines; and 7-hydroxy-9,9-dimethyl-9H-acridin-2-one and its derivatives. Preferred two electron transfer mediators include 3-phenylimino-3H-phenothiazines (PIPT) and 3-phenylimino-3H-phenoxazines (PIPO). More preferred two electron mediators include the carboxylic acid or salt, such as ammonium salts, of phenothiazine derivatives. At present, especially preferred two electron mediators include (E)-2-(3H-phenothiazine-3-ylideneamino)benzene-1,4-disulfonic acid, (E)-5-(3H-phenothiazine-3-ylideneamino)isophthalic acid, ammonium (E)-3-(3H-phenothiazine-3-ylideneamino)-5-carboxybenzoate, and combinations thereof. Examples of additional two electron mediators include the electro-active organic molecules described in U.S. Pat. Nos. 5,393,615; 5,498,542; and 5,520,786.

The reagent composition also may include a substantially water-soluble enzyme system having a unit activity range as specified by the manufacturer from about 0.1 active unit per microliter (μL) of the reagent composition to about 10 active units per μL of the reagent composition, more preferably from about 1 active unit per μL of the reagent composition to about 2 active units per μL of the reagent composition. As the solid weight of the enzyme required to provide a specific unit activity can vary substantially by formulation batch and manufacturer, the unit activity provided by the manufacturer for a specific weight of the dry enzyme composition is preferably used to determine the addition amount.

Preferable enzymes for use in the enzyme system of the reagent composition include alcohol dehydrogenase, lactate dehydrogenase, β-hydroxybutyrate dehydrogenase, glucose-6-phosphate dehydrogenase, glucose dehydrogenase, formaldehyde dehydrogenase, malate dehydrogenase, and 3-hydroxysteroid dehydrogenase. Preferable enzyme systems are oxygen independent, thus not substantially oxidized by oxygen.

One such oxygen independent enzyme family is glucose dehydrogenase (GDH). Using different co-enzymes or co-factors, GDH may be mediated in a different manner by different mediators. Depending on their association with GDH, a co-factor, such as flavin adenine dinucleotide (FAD), can be tightly held by the host enzyme, such as in the case of FAD-GDH; or a co-factor, such as Pyrroloquinolinequinone (PQQ), may be covalently linked to the host enzyme, such as with PQQ-GDH. The co-factor in each of these enzyme systems may either be permanently held by the host enzyme or the co-enzyme and the apo-enzyme may be re-constituted before the enzyme system is added to the reagent composition. The co-enzyme also may be independently added to the host enzyme moiety in the reagent composition to assist in the catalytic function of the host enzyme, such as in the cases of nicotinamide adenine dinucleotide $NAD/NADH^+$ or nicotinamide adenine dinucleotide phosphate $NADP/NADPH^+$.

Conventional reagent compositions for biosensor sensor strips have used multiple types of water-insoluble solid particles to adjust the rheology or viscosity of the compositions. Conventional reagent compositions have used solid silica particles having their surfaces modified to provide both hydrophobic and hydrophilic characteristics, such as described in U.S. Pat. No. 5,951,836. The solid particles having hydrophilic interiors and modified hydrophobic exteriors are broken to expose the hydrophilic interiors. These solid particles, whether intact or broken, directly contrast with the porous particles previously described, which include pores providing an interior volume to the particles and do not require modification with hydrophobicity enhancers.

Unlike solid particles, porous particles allow for the small, water-soluble constituents of the reagent composition to enter the pore structure, while excluding larger water-soluble constituents, such as the enzyme and polymeric material. Thus, during formation of the reagent composition suspension, the water-solubilized mediator may enter the pores. When dried, the mediator, buffer, and surfactant are believed to remain in the pores of the particles, while the larger polymeric material or materials and enzyme system reside external to the pores of the particles.

The enzyme and polymeric material or materials typically have dimensions above the 5 nanometer (nm) range, while the glucose and ferricyanide molecules typically have dimensions in the under 1 nm range. Thus, preferable pore sizes for the porous particles are less than about 5 nm. Other pore sizes may be used, based on that required to at least partially exclude the polymeric material or materials and enzyme, while allowing the mediator and analyte to enter.

Figure 3:
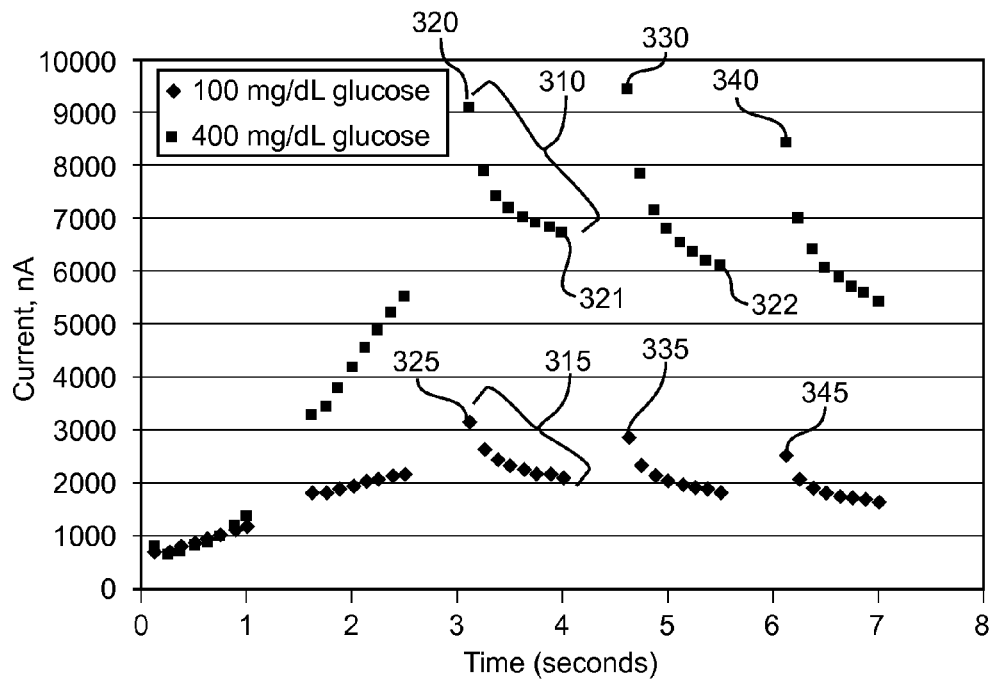
FIG. 3 shows the output signal from a biosensor strip using a reagent composition including solid clay particles.

FIG. 3 shows the output signals from biosensor sensor strips including blood samples having glucose concentrations of either 100 or 400 mg/dL. The binder used for the reagent compositions of the sensor strips included solid clay particles. The clay was an organo/clay tetra-alkyl ammonium bentonite, such as available as BENTONE EW from NL Chemicals, Brussels, Belgium. The signal input to the sensor strip by the measurement device was a gated amperometric pulse sequence that included five pulsed excitations separated by four relaxations, such as described in U.S. Patent Pub. 2008/0173552. The excitations were about 1 second in duration and the relaxations were about 0.5 second in duration. Eight output current values were recorded during each excitation.

To correlate the output current values from the input signal with the analyte concentration of the sample, the initial current value from the excitation is preferably greater than those that follow in the decay. The output signals from the sensor strips of FIG. 3 did not show an initial high current value that decays thereafter until about three seconds after the blood sample was introduced to the strip. Thus, the first output currents having a high initial current value followed by decaying current values were observed in output currents 310 for the 400 mg/dL sample and in output currents 315 for the 100 mg/dL sample.

To correlate the output current values from the input signal to the analyte concentration of the sample, different sample analyte concentrations also preferably show a substantially constant difference between output signal current values. Thus, the current difference between the 100 and 400 mg/dL glucose samples of FIG. 3 preferably should be substantially the same, with the 400 mg/dL current values being higher. However, the output signals from the sensor strips of FIG. 3 did not show a substantially constant difference between current values for the 100 and 400 mg/dL glucose concentration blood samples until between six and seven seconds had passed. This was seen when the initial current values from the 400 mg/dL sample (320, 330, and 340) were compared with the initial current values from the 100 mg/dL sample (325, 335, and 345). From FIG. 3, the current difference between current values 330 and 335 was greater than the current difference observed between current values 320 and 325, establishing that correlation of these output current values to the analyte concentration of the sample would result in inaccuracies. It was not until between six and seven seconds had passed after introduction of the sample to the sensor strip that a substantially constant difference between output signal current values 340 and 345 was observed.

Preferably, the output current value or values correlated with the analyte concentration of the sample also are taken from a decay including current data reflecting the maximum kinetic performance of the sensor strip. The kinetics of the redox reaction underlying the output currents are affected by multiple factors. These factors may include the rate at which the reagent composition rehydrates, the rate at which the enzyme system reacts with the analyte, the rate at which the enzyme system transfers electrons to the mediator, and the rate at which the mediator transfers electrons to the electrode. Of these and other kinetic factors affecting the output currents, the rate at which the reagent composition rehydrates is believed to have the greatest influence.

The maximum kinetic performance of the sensor strip may be reached during an excitation of a gated amperometric pulse sequence when the initial current value of an excitation having decaying current values is the greatest initial current value obtained for the multiple excitations. Preferably, the maximum kinetic performance of a sensor strip is reached when the last in time current value obtained for an excitation having decaying current values is the greatest last in time current value obtained for the multiple excitations. More preferably, the maximum kinetic performance of a sensor strip is reached during at time period from when the initial current value of an excitation having decaying current values is the greatest initial current value obtained for the multiple excitations to when a last in time current value obtained for the same excitation is the greatest last in time current value obtained for the multiple excitations.

The gated amperometric pulse sequence used to determine the maximum kinetic performance of a sensor strip includes at least five duty cycles, where the excitations are 0.4 second in duration and the relaxations are one second in duration, include zero current flow through the sample, and are provided by an open circuit. At least three output current values are measured during each excitation. The potential input to the sensor strip is held substantially constant, at 250 mV and the sample temperature is at 23° C.

In FIG. 3, for a sensor strip using a solid clay particle reagent composition, and including a 100 mg/dL glucose sample, the output currents reached a maximum kinetic performance during the excitation decay including the output currents 315, between 3 and 4 seconds from the introduction of the sample to the sensor strip. This was established as both the greatest initial and the greatest last in time current values obtained from an excitation having decaying current values were present in the output currents 315.

However, for the sensor strip in FIG. 3 including 400 mg/dL of glucose, the greatest last in time current value obtained from an excitation having decaying current values was current value 321 in the output currents 310, while the greatest initial current value was the current value 330 from the following excitation decay. Thus, for the higher 400 mg/dL glucose concentration sample of FIG. 3, maximum kinetic performance was not reached until between about four to about five seconds had passed from introduction of the sample to the sensor strip. As the greatest initial current value from an excitation having decaying current values was not the current value 320, but the later-observed current value 330, the reaction had not reached maximum kinetic performance until sometime after three seconds had passed from introduction of the sample to the sensor strip. Similarly, as the last in time current value 322 was not the greatest observed from an excitation having decaying current values, the reaction had passed the point of maximum kinetic performance shortly after five seconds had passed from introduction of the sample to the sensor strip.

Figure 4:
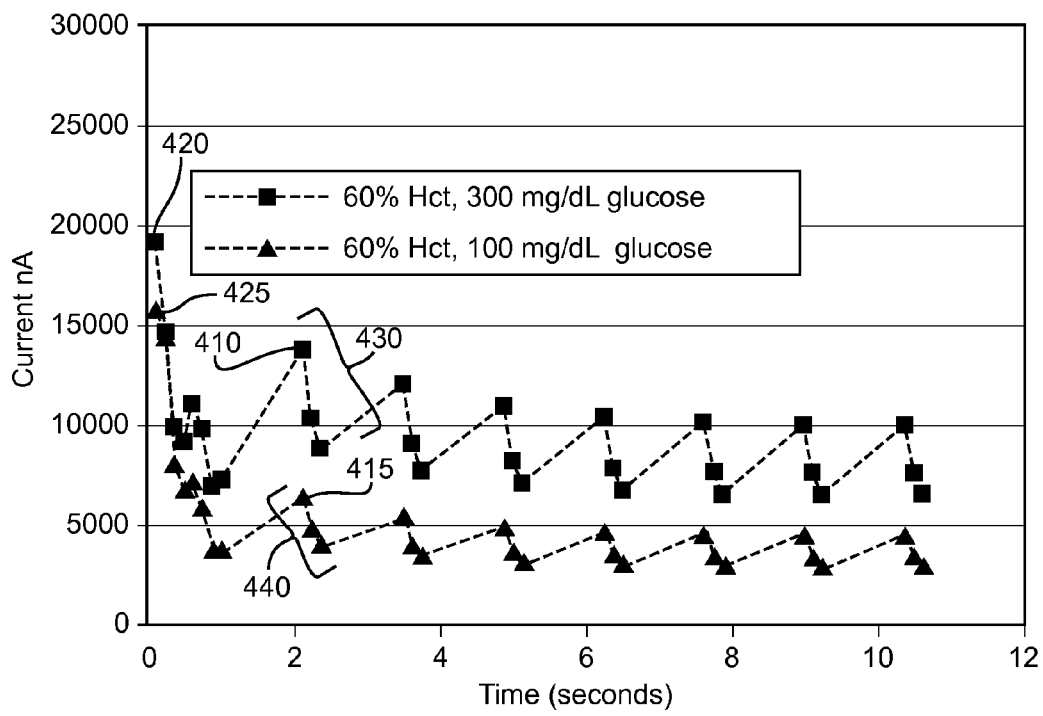
FIG. 4 shows the output signal from a biosensor strip using a reagent composition including porous silica particles.

In contrast to the output signals from the solid clay formulations of FIG. 3, FIG. 4 shows the output signals obtained from biosensor sensor strips using a reagent composition including porous silica particles, as described with regard to Example 1, below. The signal input to the sensor strip by the measurement device was a gated amperometric pulse sequence including eight excitations separated by seven relaxations, such as described in U.S. Patent Pub. 2008/0173552. The second through eighth excitations were about 0.4 second in duration, and the second through seventh relaxations were about 1 second in duration. Three output current values were recorded during the second through eighth excitations.

A substantially constant difference between the 100 and 300 mg/dL glucose concentration blood samples including 60% hematocrit (v/v) was observed within two seconds for output current values 410 (300 mg/dL) and 415 (100 mg/dL), allowing for the glucose concentration of the sample to be determined within about three seconds or less. Furthermore, the initial current values recorded about 125 milliseconds (ms) after introducing the sample to the sensor strip were separated, with the higher concentration 300 mg/dL initial current value 420 being greater than the 100 mg/dL initial current value 425. The excitation current values also decreased from the first excitation, effectively eliminating the first two seconds of the FIG. 3 analysis, during which time the output current values from the first two excitations were increasing. Thus, the output signals from the porous particle reagent compositions of FIG. 4 provided current values useful for correlation with the glucose concentration of the blood sample after about two seconds had passed from introduction of the sample to the sensor strip.

The results obtained from the reagent composition including porous particles of FIG. 4 also contrasted with the results obtained from the reagent composition including the solid particles of FIG. 3, where during the first second of the output signal in FIG. 3, the 100 and 400 mg/dL output current values were nearly identical. This result suggested that the redox reaction between the glucose analyte, enzyme system, and mediator of the reagent composition including the solid particles of FIG. 3 had not begun to any substantial degree until about two seconds passed after introduction of the sample to the sensor strip. This enhanced performance of the porous particle reagent composition is believed attributable to an enhanced availability of the reagents to the sample provided by the porous particles.

With regard to the maximum kinetic performance of sensor strips including the porous particle reagent composition, the output current values of FIG. 4 established that maximum kinetic performance was obtained for both the 100 and 300 mg/dL glucose samples within from about 2 to about 2.2 seconds of introducing the sample to the sensor strip. This was established because current values 430 included the greatest initial and greatest last current values for the 300 mg/dL sample, and current values 440 included the greatest initial and greatest last current values for the 100 mg/dL sample.

Unlike the solid clay particle reagent composition of FIG. 3, the porous particle reagent composition of FIG. 4 provided maximum kinetic performance within substantially the same about 2 to about 2.2 second time period from sample introduction for both the 100 and 300 mg/dL glucose samples. Thus, the porous particle reagent composition provided for maximum kinetic performance of the sensor strip in less than about three seconds of sample introduction, and preferably within less than about 2.5 seconds of sample introduction. More preferably, maximum kinetic performance is observed within from about two to about 2.5 seconds of introducing the sample to the sensor strip. An additional benefit of the porous particle reagent composition is that the time at which maximum kinetic performance of the reaction is observed is not substantially dependent on the analyte concentration of the sample, as was the case for the solid clay particle reagent compositions observed in FIG. 3.

Figure 5:
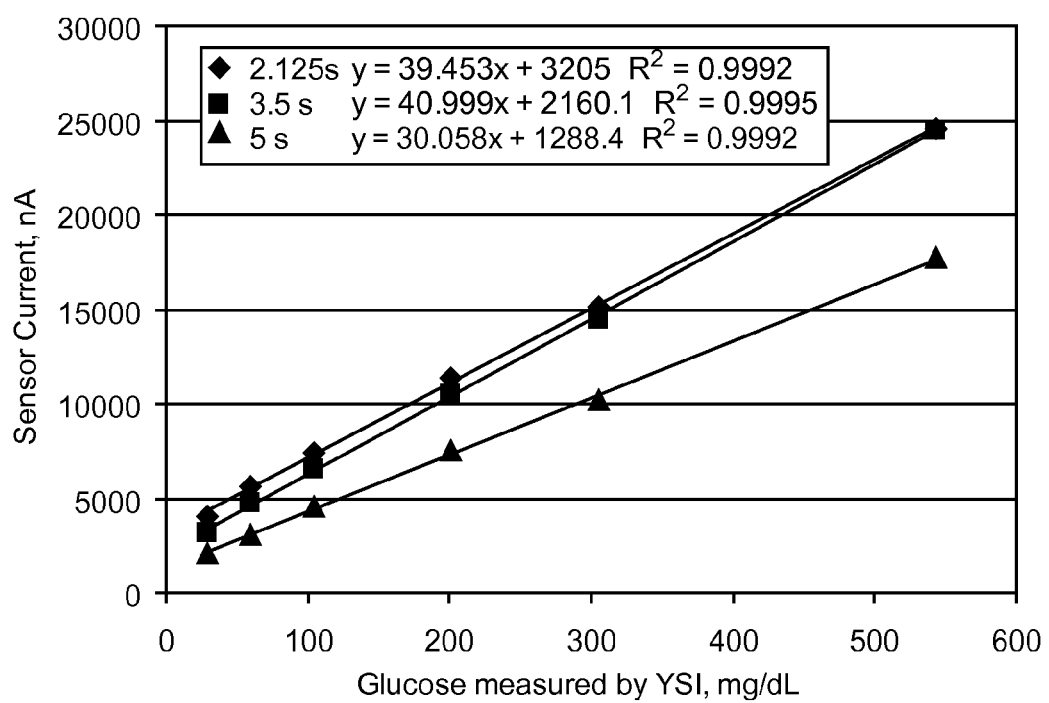
FIG. 5 is a dose response plot showing the substantially linear dose response provided by the porous particle reagent composition within about two seconds of introducing the blood sample to the strip.

FIG. 5 is a dose response plot showing the substantially linear dose response provided by the porous particle reagent composition within about two seconds of introducing a blood sample to a sensor strip. The blood samples were prepared by drawing blood from two males and two females having the same blood type into sodium heparinized tubes previously incubated at about 23-25° C. for about 24±2 hours. After incubation, the blood was combined and the hematocrit level adjusted to about 41-43%. The blood was then divided into six aliquots and a 20% glucose stock solution was used to create a different glucose concentration in each aliquot.

Each of the six aliquots was introduced to ten sensor strips and the output current values for each aliquot from the ten sensor strips were averaged and plotted against the reference glucose concentration determined for each aliquot in FIG. 5. Reference concentration values were obtained with a reference instrument, such as the YSI 2300 STAT PLUS™ available from YSI Inc., Yellow Springs, Ohio. The sensor strips used a reagent composition including porous silica particles, as described with regard to Example 1, below. The signal input to the sensor strips by the measurement device was a gated amperometric pulse sequence, as previously described with regard to FIG. 4. The output currents selected for averaging were the first recorded during the excitations at about 2.125, 3.5, and 5 seconds. As seen in the $R^2$ values for each line, the linearity of the glucose concentration values obtained from about 50 to about 550 mg/dL of glucose at 2.125 seconds were substantially equivalent, at an $R^2$ of 0.999, to the linearity of the glucose concentration values determined at 3 and 5 seconds for different glucose concentrations.

Thus, sensor strips using a reagent composition including porous silica particles provided current values for correlation with the analyte concentration of the samples within about 2.2 seconds or less of introducing the sample to the sensor strip. Preferable time periods for obtaining output current values for correlation with the analyte concentration of the sample are less than about 5 seconds, and more preferably less than about 3 seconds, of introducing the sample to the sensor strip. At present, output current values for correlation with the analyte concentration of the sample are preferably obtained within about 0.4 to about 5 seconds, more preferably within about 1.7 to about 2.7 seconds of introducing the sample to the sensor strip. Preferably, for glucose analysis in whole blood, concentration values determined from about 50 to about 550 mg/dL of glucose have a $R^2$ correlation value of at least 0.85, more preferably, at least 0.90.

Figure 6:
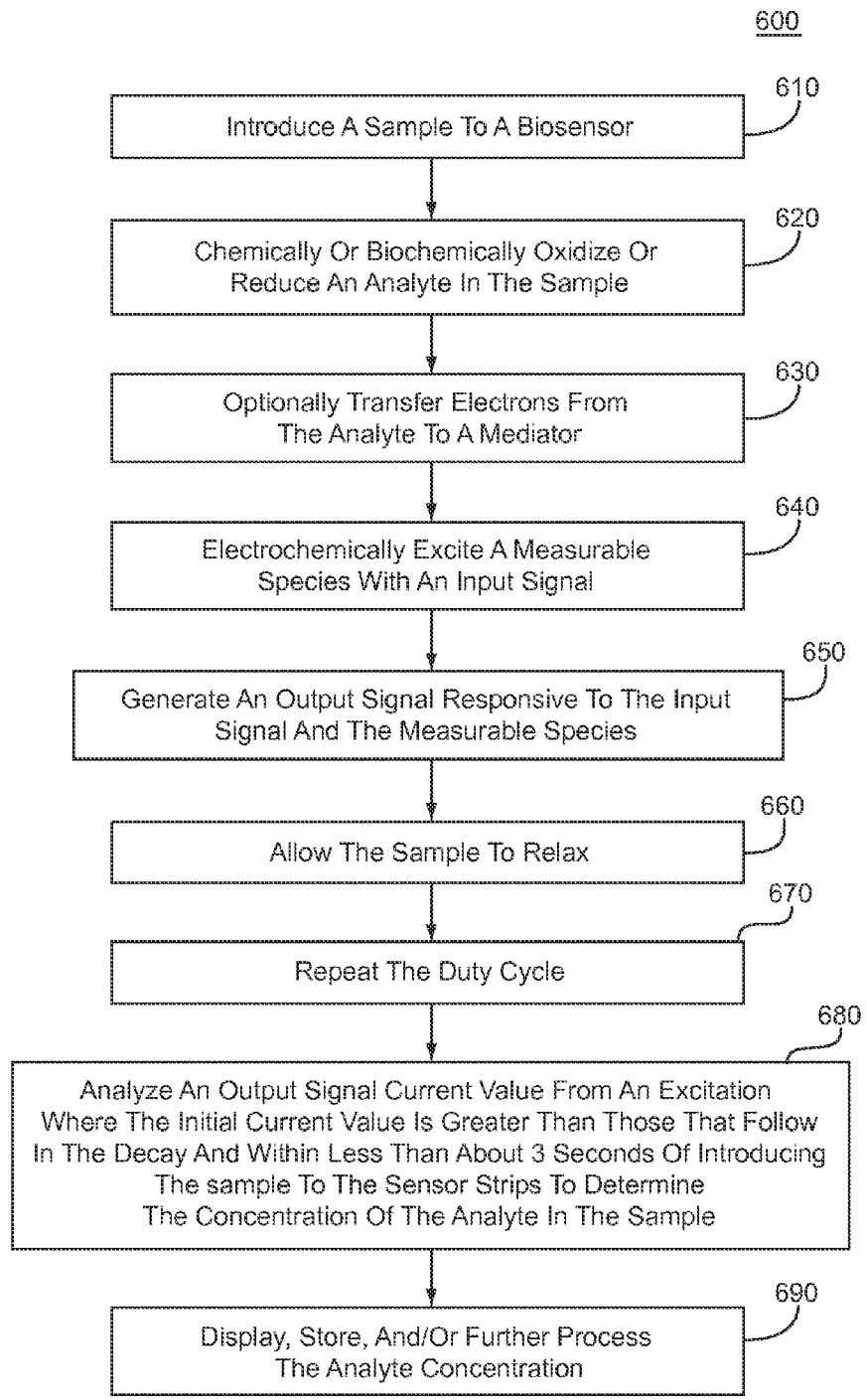
FIG. 6 represents an electrochemical analytic method for determining the presence and/or concentration of an analyte in a sample contacting a porous particle reagent composition.

FIG. 6 represents an electrochemical analytic method 600 for determining the presence and/or concentration of an analyte in a sample contacting a reagent composition including porous particles. In 610, the sample is introduced to the biosensor including the porous particle reagent composition. In 620, a portion of the analyte in the sample undergoes a redox reaction. In 630, electrons are optionally transferred from the analyte to a mediator. In 640, a measurable species is electrochemically excited with an input signal. In 650, an output signal is generated and measured. In 660, the sample is allowed to relax, and in 170, at least one additional excitation pulse is input. In 680, the presence and/or concentration of the sample is determined from the output signal, and in 690, the concentration may be displayed, stored, or the like.

In 610, the sample is introduced to the sensor portion of the biosensor, such as a sensor strip. The sensor strip includes at least one working and at least one counter electrode. The electrodes may include one or more reagent layers, with at least one reagent layer formed from a reagent composition including porous particles. The same reagent composition may be used on the working and counter electrodes, or different reagent compositions may be used to facilitate the operation of the electrodes. For example, the reagent composition at the working electrode may facilitate the reaction of the analyte, e.g. enzyme system and mediator, while the reagent composition at the counter electrode may facilitate the free flow of electrons between the sample and the surface of the electrode, e.g. a reducible species.

In 620, a portion of the analyte present in the sample is chemically or biochemically oxidized or reduced, such as by an oxidoreductase. This occurs as the sample hydrates the reagents in the porous particle reagent composition. Upon oxidation or reduction, electrons optionally may be transferred between the analyte and a mediator in 630. Thus, an ionized measurable species is formed, such as from the analyte or a mediator.

In 640, a measurable species, which may be the charged analyte from 620 or the charged mediator from 630, is electrochemically excited (oxidized or reduced) with an input signal. Input signals may be electrical signals, such as current or potential, that pulse or turn on and off at a set sequence. The input signal is a sequence of excitation pulses separated by relaxations. During an amperometric pulse, the electrical potential applied during the excitation is preferably applied at a substantially constant voltage and polarity throughout its duration. This directly contrasts to some conventional excitations where the voltage is changed or "swept" through multiple voltage potentials and/or polarities during data recordation.

Input signals may have one or more pulse interval. A pulse interval is the sum of a pulse and the relaxation constituting a duty cycle. Each pulse has an amplitude and a width. The amplitude indicates the intensity of the potential, the current, or the like of the electrical signal. The amplitude may vary or be substantially constant, such as during amperometry, during the pulse. The pulse width is the time duration of the pulse. The pulse widths in an input signal may vary or be substantially the same. Each relaxation has a relaxation width, which is the time duration of the relaxation. The relaxation widths in an input signal may vary or be substantially the same.

By adjusting the width of the excitation and relaxation of the duty cycles, gated input signals may increase the accuracy and/or precision of the analysis. Preferable input signals include at least 2, 3, 4, or 8 duty cycles applied during less than 2, 3, or 5 seconds. More preferably, at least 2 duty cycles are applied within 3 seconds. Preferably, the width of each excitation pulse is independently selected from between 0.1 and 2 seconds and more preferably from between 0.2 and 1 second. At present, especially preferred input signal pulse widths are independently selected from between 0.3 and 0.8 seconds. Preferable pulse intervals are in the range of less than 3, 2.5, or 1.5 seconds. At present, input signals having pulse widths of 0.3 to 0.5 second and pulse intervals from 0.7 to 2 seconds are especially preferred. The input signal may have other pulse widths and intervals.

In 650, the biosensor generates an output signal in response to the measurable species and the input signal. The output signal, such as one or more current values, may be measured continuously or intermittently and may be recorded as a function of time. Suitable output signals may include those that reach a steady-state and those that are transient. Steady-state current values are observed when the current change with respect to time is substantially constant, such as within ±10 or ±5%. Transient current values decay with respect to time.

In 660, the sample undergoes relaxation. The measurement device may open the circuit through the sensor strip, thus allowing relaxation. During the relaxation 660, the current present during the excitation 640 is substantially reduced by at least one-half, preferably by an order of magnitude, and more preferably to zero. Preferably, a zero current state is provided by an open circuit or other method known to those of ordinary skill in the art to provide a substantially zero current flow. Preferably, the output signal is not recorded during the relaxation 660.

In 670, the biosensor continues to apply pulses from the input signal to the working and counter electrodes for the desired time period. The duty cycle including the excitation 640 and the relaxation 660 may be repeated or a duty cycle having different pulse widths and/or intervals may be applied.

In 680, the biosensor analyzes an output signal current value by correlating one or more current values with the analyte concentration of the sample. Preferably, the output current value that is correlated with the analyte concentration of the sample is recorded from an excitation where the initial current value is greater than those that follow in the decay and within less than about 3 seconds of introducing the sample to the sensor strip in 610. More preferably, the output current value that is correlated with the analyte concentration of the sample is obtained within less than about 3 seconds of introducing the sample to the sensor strip in 610 and is the first current value recorded from an excitation where the current values that follow the first current value decrease. Even more preferably, the output current value that is correlated with the analyte concentration of the sample is obtained within less than about 3 seconds of introducing the sample to the sensor strip in 610, is the first current value recorded from an excitation where the current values that follow the first current value decrease, and is obtained during the maximum kinetic performance of the sensor strip. Additional current, time, and/or other values also may be analyzed. In 690, the analyte concentration value may be displayed, stored for future reference, and/or used for additional calculations.

Figure 7:
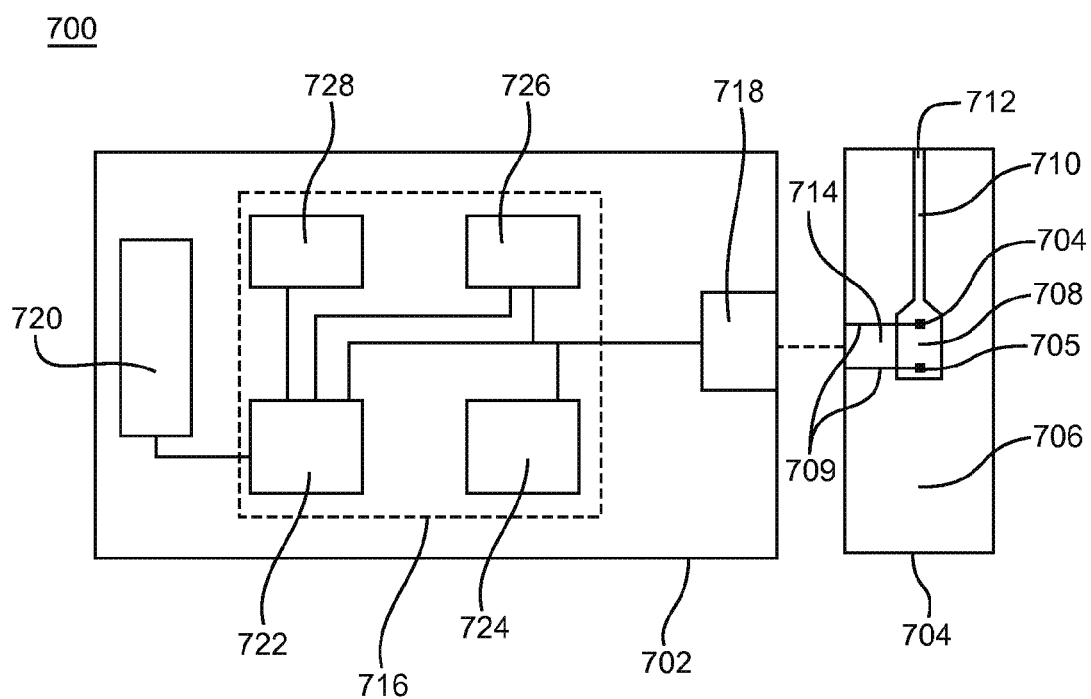
FIG. 7 depicts a schematic representation of a biosensor that determines an analyte concentration in a sample of a biological fluid using a gated amperometric input signal.

FIG. 7 depicts a schematic representation of a biosensor 700 that determines an analyte concentration in a sample of a biological fluid using a gated amperometric input signal. The biosensor 700 includes a measurement device 702 and a sensor strip 704, which may be implemented in any analytical instrument, including a bench-top device, a portable or handheld device, or the like. The biosensor 700 may be utilized to determine analyte concentrations, including those of glucose, uric acid, lactate, cholesterol, bilirubin, and the like. While a particular configuration is shown, the biosensor 700 may have other configurations, including those with additional components.

The sensor strip 704 has a base 706 forming a reservoir 708 and a channel 710 with an opening 712. The reservoir 708 and the channel 710 may be covered by a lid with a vent. The reservoir 708 defines a partially-enclosed volume. The reservoir 708 may contain a composition that assists in retaining a liquid sample such as water-swellable polymers or porous polymer matrices. Reagents may be deposited in the reservoir 708 and/or channel 710. The reagent composition used to form the working electrode 704 includes porous particles and may include one or more enzyme system, mediator, and like species. The counter electrode 705 may be formed using the same or a different reagent composition, preferably one lacking an enzyme system. The sensor strip 704 also may have a sample interface 714 disposed adjacent to the reservoir 708. The sample interface 714 may partially or completely surround the reservoir 708. The sensor strip 704 may have other configurations.

The sample interface 714 has conductors 709 connected to the working electrode 704 and the counter electrode 705. The electrodes may be substantially in the same plane or in more than one plane. The electrodes 704, 705 may be disposed on a surface of the base 706 that forms the reservoir 708. The electrodes 704, 705 may extend or project into the reservoir 708. A dielectric layer may partially cover the conductors 709 and/or the electrodes 704, 705. The sample interface 714 may have other electrodes and conductors.

The measurement device 702 includes electrical circuitry 716 connected to a sensor interface 718 and a display 720. The electrical circuitry 716 includes a processor 722 connected to a signal generator 724, an optional temperature sensor 726, and a storage medium 728.

The signal generator 724 provides an electrical input signal to the sensor interface 718 in response to the processor 722. The electrical input signal may be transmitted by the sensor interface 718 to the sample interface 714 to apply the electrical input signal to the sample of the biological fluid. The electrical input signal may be a potential or current and may be applied in multiple pulses, sequences, or cycles. The signal generator 724 also may record an output signal from the sensor interface as a generator-recorder.

The optional temperature sensor 726 determines the temperature of the sample in the reservoir of the sensor strip 704. The temperature of the sample may be measured, calculated from the output signal, or assumed to be the same or similar to a measurement of the ambient temperature or the temperature of a device implementing the biosensor system. The temperature may be measured using a thermister, thermometer, or other temperature sensing device. Other techniques may be used to determine the sample temperature.

The storage medium 728 may be a magnetic, optical, or semiconductor memory, another storage device, or the like. The storage medium 728 may be a fixed memory device, a removable memory device, such as a memory card, remotely accessed, or the like.

The processor 722 implements the analyte analysis and data treatment using computer readable software code and data stored in the storage medium 728. The processor 722 may start the analyte analysis in response to the presence of the sensor strip 704 at the sensor interface 718, the application of a sample to the sensor strip 704, in response to user input, or the like. The processor 722 directs the signal generator 724 to provide the electrical input signal to the sensor interface 718. The processor 722 may receive the sample temperature from the optional temperature sensor 726. The processor 722 receives the output signal from the sensor interface 718. The output signal is generated in response to the redox reaction of the analyte in the reservoir 708.

The processor 722 preferably measures the output signal to obtain a current value from an excitation where the initial current value is greater than those that follow in the decay and within less than about 3 seconds of introducing the sample to the sensor strip 704. More preferably, the processor 722 measures the output signal to obtain a current value within less than about 3 seconds of introducing the sample to the sensor strip in 704 and obtains the first current value recorded from an excitation where the current values that follow the first current value continuously decrease. Even more preferably, the processor 722 measures the output signal to obtain a current value within less than about 3 seconds of introducing the sample to the sensor strip in 704, to obtain the first current value recorded from an excitation where the current values that follow the first current value continuously decrease, and to obtain a current value during the maximum kinetic performance of the sensor strip.

The one or more obtained current value is correlated with the analyte concentration of the sample using one or more correlation equations in the processor 722. The results of the analyte analysis may be output to the display 720 and may be stored in the storage medium 728. Preferably, the results of the analyte analysis are output to the display 720 within at most five seconds of introducing the sample to the sensor strip, more preferably the results are output to the display 720 within at most three seconds of introducing the sample to the sensor strip.

The correlation equations relating analyte concentrations and output current values may be represented graphically, mathematically, a combination thereof, or the like. The correlation equations may be represented by a program number (PNA) table, another look-up table, or the like that is stored in the storage medium 728. Instructions regarding implementation of the analyte analysis may be provided by the computer readable software code stored in the storage medium 728. The code may be object code or any other code describing or controlling the functionality described herein. The data from the analyte analysis may be subjected to one or more data treatments, including the determination of decay rates, K constants, ratios, and the like in the processor 722.

The sensor interface 718 has contacts that connect or electrically communicate with the conductors 709 in the sample interface 714 of the sensor strip 704. The sensor interface 718 transmits the electrical input signal from the signal generator 724 through the contacts to the conductors 709 in the sample interface 714. The sensor interface 718 also transmits the output signal from the sample through the contacts to the processor 722 and/or signal generator 724.

The display 720 may be analog or digital. The display may be a LCD adapted to display a numerical reading.

In use, a sample for analysis is transferred into the reservoir 708 by introducing the sample to the opening 712. The sample flows through the channel 710, filling the reservoir 708 while expelling the previously contained air. The sample chemically reacts with the reagents deposited in the channel 710 and/or reservoir 708. Preferably, the sample is a fluid, more preferably, a liquid.

The sensor strip 702 is disposed adjacent to the measurement device 702. Adjacent includes positions where the sample interface 714 is in electrical communication with the sensor interface 718. Electrical communication includes wired or wireless transfer of input and/or output signals between contacts in the sensor interface 718 and conductors 709 in the sample interface 714.

The following examples are provided to illustrate one or more preferred embodiments of the invention. Numerous variations can be made to the following examples that lie within the scope of the invention.

EXAMPLES

The constituents combined to form the following reagent compositions were obtained from multiple sources. In general, PVA, Citric Acid, $K_2HPO_4$, Potassium Ferricyanide, and the MEGA 8 surfactant were obtained from Sigma-Aldrich, St. Louis, Mo. The Surfynol 485 surfactant was obtained from Air Products, Allentown, Pa. The enzyme systems were obtained from Amano Enzymes, Nagoya, Japan. The Porous Particle Silica Slurry was obtained from Grace Davison, East Chicago, Ind.

Example 1

Reagent Composition I

A reagent composition was prepared by combining the constituents from Table I, below, in 38.67 g of water. The porous particle slurry included about 25.3% porous particles, had a pH of 7.5, an average diameter of the particles in the mixture of about 4 μm (D99.9 by Horiba LA-910), an average pore volume per particle of about 0.74 mL/g ($N_2$ adsorption), and an average surface area per particle of about 163 m²/g ($N_2$ adsorption). For examples 2-9, the slurry included about 29.9% porous particles, had a pH of 4, an average diameter of the particles in the mixture of about 1.20 μm (D99.9 by Horiba LA-910), and an average pore volume per particle of about 0.70 mL/g ($N_2$ adsorption).

TABLE I

| Reagent Composition Constituent | Weight in grams |
| --- | --- |
| Polyvinyl Alcohol (Mw = 30,000-50,000, ~87% hydrolyzed) | 0.6 |
| Porous Silica Particle Slurry (25% w/w in water) | 6 |
| 100 mM Citrate Buffer, pH = 5 | 50 |
| MEGA 8 (10% w/w in water) | 2 |
| Potassium Ferricyanide | 1.98 |
| FAD-GDH Enzyme System | 0.75 |

TABLE I-continued

| Reagent Composition Constituent | Weight in grams |
| --- | --- |
| (Unit Activity of about 1.5 units/μL of the reagent composition) | (solid weight as obtained from manufacturer) |

Example 2

Reagent Composition II

A reagent composition was prepared lacking the enzyme system by combining the constituents from Table II, below, in 26.92 g of water.

TABLE II

| Reagent Composition Constituent | Weight in grams |
| --- | --- |
| Polyvinyl Alcohol (Mw = 30,000-50,000, ~87% hydrolyzed) | 0.5 |
| Hydroxyethylene Cellulose (Mw = 300,000) | 0.2 |
| Porous Silica Particle Slurry (30% w/w in water) | 6 |
| Citric Acid | 0.14 |
| $K_2HPO_4$ | 0.26 |
| SURFYNOL 485 | 0.01 |
| Potassium Ferricyanide | 0.96 |

Example 3

Reagent Composition III

A reagent composition was prepared lacking the enzyme system by combining the constituents from Table III, below, in 29.18 g of water.

TABLE III

| Reagent Composition Constituent | Weight in grams |
| --- | --- |
| Polyvinyl Alcohol (Mw = 30,000-50,000, ~87% hydrolyzed) | 0.1 |
| Hydroxyethylene Cellulose (Mw = 300,000) | 0.15 |
| Sodium Poly Acrylic Acid (Mw = 7,000) | 0.15 |
| Porous Silica Particle Slurry (30% w/w in water) | 2 |
| Citric Acid | 0.14 |
| $K_2HPO_4$ | 0.26 |
| SURFYNOL 485 | 0.01 |
| Potassium Ferricyanide | 0.96 |

Example 4

Reagent Composition IV

A reagent composition was prepared lacking the enzyme system by combining the constituents from Table IV, below, in 27.42 g of water.

TABLE IV

| Reagent Composition Constituent | Weight in grams |
| --- | --- |
| Polyvinyl Alcohol (Mw = 30,000-50,000) | 0.05 |
| Hydroxyethylene Cellulose (Mw = 300,000) | 0.15 |
| Porous Silica Particle Slurry (30% w/w in water) | 1 |
| Citric Acid | 0.14 |
| $K_2HPO_4$ | 0.26 |
| SURFYNOL 485 | 0.01 |
| Potassium Ferricyanide | 0.96 |

Example 5

Reagent Composition V

A reagent composition was prepared lacking the enzyme system by combining the constituents from Table V, below, in 27.37 g of water.

TABLE V

| Reagent Composition Constituent | Weight in grams |
| --- | --- |
| Polyvinyl Alcohol (Mw = 30,000-50,000) | 0.1 |
| Hydroxyethylene Cellulose (Mw = 300,000) | 0.15 |
| Porous Silica Particle Slurry (30% w/w in water) | 1 |
| Citric Acid | 0.14 |
| $K_2HPO_4$ | 0.26 |
| SURFYNOL 485 | 0.01 |
| Potassium Ferricyanide | 0.96 |

Example 6

Reagent Composition VI

A reagent composition was prepared lacking the enzyme system by combining the constituents from Table VI, below, in 26.37 g of water.

TABLE VI

| Reagent Composition Constituent | Weight in grams |
| --- | --- |
| Polyvinyl Alcohol (Mw = 30,000-50,000) | 0.1 |
| Hydroxyethylene Cellulose (Mw = 300,000) | 0.15 |
| Porous Silica Particle Slurry (30% w/w in water) | 2 |
| Citric Acid | 0.14 |
| $K_2HPO_4$ | 0.26 |
| SURFYNOL 485 | 0.01 |
| Potassium Ferricyanide | 0.96 |

Example 7

Reagent Composition VII

A reagent composition was prepared lacking the enzyme system by combining the constituents from Table VII, below, in 27.28 g of water.

TABLE VII

| Reagent Composition Constituent | Weight in grams |
| --- | --- |
| Polyvinyl Alcohol (Mw = 30,000-50,000) | 0.15 |
| Hydroxyethylene Cellulose (Mw = 300,000) | 0.15 |
| Porous Silica Particle Slurry (30% w/w in water) | 2 |
| Citric Acid | 0.14 |
| $K_2HPO_4$ | 0.26 |
| SURFYNOL 485 | 0.01 |
| Potassium Ferricyanide | 0.96 |

Example 8

Reagent Composition VIII

A reagent composition was prepared lacking the enzyme system by combining the constituents from Table VIII, below, in 26.28 g of water.

TABLE VIII

| Reagent Composition Constituent | Weight in grams |
| --- | --- |
| Polyvinyl Alcohol (Mw = 30,000-50,000) | 0.15 |
| Hydroxyethylene Cellulose (Mw = 300,000) | 0.15 |
| Porous Silica Particle Slurry (30% w/w in water) | 3 |
| Citric Acid | 0.14 |
| $K_2HPO_4$ | 0.26 |
| SURFYNOL 485 | 0.01 |
| Potassium Ferricyanide | 0.96 |

Example 9

Reagent Composition IX

A reagent composition was prepared lacking the enzyme system by combining the constituents from Table IX, below, in 29.13 g of water.

TABLE IX

| Reagent Composition Constituent | Weight in grams |
| --- | --- |
| Polyvinyl Alcohol (Mw = 30,000-50,000) | 0.15 |
| Hydroxyethylene Cellulose (Mw = 300,000) | 0.15 |
| Sodium Poly Acrylic Acid (Mw = 7,000) | 0.15 |
| Porous Silica Particle Slurry (30% w/w in water) | 2 |
| Citric Acid | 0.14 |
| $K_2HPO_4$ | 0.26 |
| SURFYNOL 485 | 0.01 |
| Potassium Ferricyanide | 0.96 |

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. An electrode for a biosensor, comprising:
   at least one conductor; and
   at least one reagent composition disposed on the conductor, the reagent composition comprising:
   porous particles having an average diameter from 0.05 micrometer to 10 micrometer and a void volume of at least 20% (v/v);
   from about 0.5% to about 10% (w/w) of at least one mediator;
   at least one polymeric material; and
   at least one enzyme system.

2. The electrode of claim 1, where the reagent composition is formed from drying water from a colloidal suspension of the reagent composition.

3. The electrode of claim 1, the reagent composition further comprising from about 0.01% to about 1% (w/w) of at least one surfactant.

4. The electrode of claim 1, the porous particles having an average pore volume from about 0.5 to about 1 milliliter per gram.

5. The electrode of claim 1, the porous particles having an average surface area from about 100 to about 200 meter$^2$ per gram.

6. A biosensor sensor strip, for determining the concentration of an analyte in a sample, comprising:
   a sensor base at least partially covered by a lid;
   at least one reservoir formed by the sensor base, where the at least one reservoir encloses at least two conductors disposed on the base; and at least one reagent composition on at least one of the conductors to form a working electrode, the at least one reagent composition comprising, porous particles having an average diameter from 0.05 micrometer to 10 micrometer and a void volume of at least 20% (v/v);

about 0.1 active unit to about 10 active units of at least one enzyme system per microliter of the at least one reagent composition, about 0.5% to about 10% (w/w) of at least one mediator, and at least one polymeric material;

where the reservoir and the at least one reagent composition provide a maximum kinetic performance of a redox reaction of an analyte with the at least one reagent composition within less than about three seconds of introducing a sample to the sensor strip; and where the maximum kinetic performance is determined with a gated amperometric pulse sequence having at least five duty cycles, where each excitation of the duty cycles is 0.4 second in duration, each relaxation of the duty cycles is one second in duration, the relaxations are provided by an open circuit, at least three output current values are measured during each excitation, the excitations have a substantially constant potential of 250 mV, and the sample temperature is 23° C.

7. The strip of claim 6, where the maximum kinetic performance of the redox reaction of the analyte with the at least one reagent composition is provided within from about 2 to about 2.5 seconds of introducing the sample to the sensor strip.

8. The strip of claim 6, where the maximum kinetic performance is reached when an initial current value obtained from an excitation having decaying current values is the greatest initial current value obtained from the at least five duty cycles.

9. The strip of claim 6, where the maximum kinetic performance is reached when a last in time current value obtained from an excitation having decaying current values is the greatest last in time current value obtained from the at least five duty cycles.

10. The strip of claim 6, where the maximum kinetic performance is reached during a time period from when an initial current value obtained from an excitation having decaying current values is the greatest initial current value obtained from the at least five duty cycles to when a last in time current value obtained from the same excitation is the greatest last in time current value obtained from the at least five duty cycles.

11. The strip of claim 6, where the analyte comprises glucose, where the sample comprises whole blood, and where the maximum kinetic performance of the redox reaction occurs within substantially the same time of introducing the sample to the sensor strip for glucose concentrations of from 100 mg/dL to 300 mg/dL in the sample.

12. The strip of claim 6, the reagent composition further comprising from about 0.01% to about 1% (w/w) of at least one surfactant.

13. The strip of claim 6, the porous particles having an average pore volume from about 0.5 to about 1 milliliter per gram.

14. The strip of claim 6, the porous particles having an average surface area from about 100 to about 200 meter$^2$ per gram.

15. A method of determining the concentration of a biological analyte, comprising:

introducing an aqueous sample including at least one biological analyte to a an electrode, the electrode comprising:

at least one conductor; and at least one reagent composition disposed on the conductor, the reagent composition comprising:

porous particles having an average diameter from 0.05 micrometer to 10 micrometer and a void volume of at least 20% (v/v);

from about 0.5% to about 10% (w/w) of at least one mediator;

at least one polymeric material; and at least one enzyme system;

rehydrating the reagent composition with the aqueous sample;

applying an input signal to the aqueous sample;

measuring at least one output signal current value within about 0.4 to about 5 seconds of introducing the aqueous sample to the reagent composition; and determining the concentration of the at least one analyte in the aqueous sample from the at least one output signal current value.

16. The method of claim 15, comprising measuring the at least one output signal current value within about 1.7 to about 2.7 seconds of introducing the aqueous sample to the reagent composition.

17. The method of claim 15, where the analyte comprises glucose, where the aqueous sample comprises whole blood, where at least two output signal current values are determined at sample glucose concentrations between about 50 mg/dL to about 550 mg/dL, and where the at least two output signal current values when correlated with reference glucose concentration values have a $R^2$ linearity value of at least 0.90.

18. The method of claim 15, further comprising measuring the at least one output signal current value during a maximum kinetic performance of a redox reaction between the reagent composition and the at least one analyte, where the maximum kinetic performance is determined with a gated amperometric pulse sequence having at least five duty cycles, and where each excitation of the duty cycles is 0.4 seconds in duration, each relaxation of the duty cycles is one second in duration, the relaxations are provided by an open circuit, at least three output current values are measured during each excitation, the excitations have a substantially constant potential of 250 mV, and the sample temperature is 23° C.

19. The method of claim 18, comprising measuring the at least one output signal current value within about 1.7 to about 2.7 seconds of introducing the aqueous sample to the reagent composition.

20. The method of claim 18, further comprising measuring the at least one output signal current value during a current decay.

21. The method of claim 15, the porous particles having an average pore volume from about 0.5 to about 1 milliliter per gram.

22. The method of claim 15, the porous particles having an average surface area from about 100 to about 200 meter$^2$ per gram.

23. The method of claim 15, further comprising outputting a determined concentration of the at least one analyte to a display within at most five seconds.

24. The method of claim 15, further comprising outputting a determined concentration of the at least one analyte to a display within at most three seconds.

* * * * *